United States Patent [19]

MacGregor et al.

[11] Patent Number: 4,628,944
[45] Date of Patent: Dec. 16, 1986

[54] CARDIAC PACING LEAD WITH BIODEGRADABLE FIXATION STRUCTURE

[75] Inventors: David C. MacGregor; Stanley H. Saulson, both of Miami, Fla.

[73] Assignee: Cordis Corporation, Miami, Fla.

[21] Appl. No.: 817,790

[22] Filed: Jan. 7, 1986

Related U.S. Application Data

[63] Continuation of Ser. No. 631,019, Jul. 17, 1984, abandoned, which is a continuation of Ser. No. 347,007, Feb. 8, 1982, abandoned.

[51] Int. Cl.$^4$ .............................................. A61N 1/05
[52] U.S. Cl. ................................ 128/785; 128/419 P
[58] Field of Search ............................... 128/784-786, 128/419 P, 642

[56] References Cited

U.S. PATENT DOCUMENTS

| | | | |
|---|---|---|---|
| 4,258,724 | 3/1981 | Balat et al. | 128/785 |
| 4,280,514 | 7/1981 | MacGregor | 128/786 |
| 4,301,815 | 11/1981 | Doring | 128/786 |
| 4,407,303 | 10/1983 | Akerstrom | 128/785 |

FOREIGN PATENT DOCUMENTS 2453840 5/1976 Fed. Rep. of Germany ...... 128/785

OTHER PUBLICATIONS

"The Cordis ... Lead", Cordis Corp., Aug. 1979.
David C. MacGregor, M.D., et al, "The Porous-Surfaced Electrode", *The Journal of Thoracic and Cardiovascular Surgery*, vol. 78, No. 2, pp. 281–291, Aug. 1979.

*Primary Examiner*—Lee S. Cohen
*Attorney, Agent, or Firm*—George H. Gerstman

[57] ABSTRACT

Disclosed is a cardiac pacing lead comprising an electrical stimulating member (electrode) with a plurality of biodegradable fins adjacent to its tip and with or without a porous metal coating. After surgical introduction, temporary fixation of the device to the surface of the cardiac wall is supplied by the fins. The device achieves permanent fixation by ingrowth of viable tissue into the interstices of the porous electrode and/or by tissue ensheathment of the distal portion of the lead. The process of permanent fixation occurs over a period of weeks during which time the fins are gradually absorbed into the blood and/or adjacent tissue. The lead can also be used to stimulate tissue other than cardiac tissue, such as nervous system tissue.

16 Claims, 7 Drawing Figures

CARDIAC PACING LEAD WITH BIODEGRADABLE FIXATION STRUCTURE

This application is a continuation of U.S. application Ser. No. 631,019, filed July 17, 1984 and now abandoned, which is a continuation of U.S. application Ser. No. 347,007, filed Feb. 8, 1982, and now abandoned.

BACKGROUND OF THE INVENTION

Electrical monitoring and stimulation of heart action is well known and has been employed to counter a variety of heart disfunctions. Such monitoring and stimulation requires a reliable means of attaching and maintaining proximity of a conducting electrode to the heart wall. This need arises, for example, in securing a pervenous cardiac pacing lead to the inside wall of the right ventricle. There have been many attempts to achieve such a means. One way is by bonding the electrode to the endocardium with an adhesive. The problem with such adhesive bonding is that it may not provide reliable anchoring of the stimulation electrode and may produce an adverse tissue reaction. Another way is by use of a smooth-surfaced harpoon-like device. Here, a temporary anchor is achieved by piercing the heart wall with an absorbable "harpoon" stored within the electrode.

A third way of attaching an electrode to the inner heart wall is by the use of a tined device. Here, the electrode is held in proximity to the wall of the heart by inert tines which extend from the lead adjacent to the electrode and form an acute angle with the electrode body. These tines maintain the electrode in electrical contact with the heart tissue. The problem with this type of tined device is that over time, the tines will stimulate fibrotic tissue growth which will make later removal of the lead more difficult and which may interfere with the pacing threshold as the tines are typically quite close to the electrode's contact point. Additionally, even after the formation of fibrosis around the electrode, the mechanical stresses on the tines, due to myocardial contractions, can cause shifts in the electrode's position and/or additional tissue reaction.

U.S. Pat. No. 4,281,669 provides novel cardiovascular devices or implants (including pacemaker electrodes) which have biocompatibility and hence reduce thrombogenic problems. The pacemaker electrode embodiment is preferably in the form of a rigid, porous metal coating on a dense coherent metal substrate with a network of interconnected pores substantially uniformly distributed throughout the coating. The rigid nature of the metal coating, the strength of the substrate-coating interface and the strength of the particle-particle bond in the coating provide excellent strength and wear resistance characteristics. The formation of a thin, smooth, firmly attached tissue coating on the porous surface allows the electrode to be incorporated into the cardiovascular system. This tissue coating is formed by a combination of colonization by nucleated cells circulating in the blood stream onto the porous surface and subsequent differentiation into other cell types plus true soft tissue ingrowth into the porous surface from adjacent body tissue thereby achieving a more secure attachment than has previously been the case.

Although the porous pacing electrode offers the advantage of improved blood tissue compatibility over a smooth pacing electrode, both require a period of several weeks to months to become firmly attached, during which time another means of attaching the lead to the heart wall is needed.

SUMMARY OF THE INVENTION

The problems of the prior art are overcome by the present invention, which provides a non-penetrating means for temporary attachment of a tissue stimulating lead to the surface of the tissue to be stimulated, said means being constituted of biodegradable material absorbable in the blood and adjacent tissue of the patient.

In a preferred form, the electrical stimulating member of a cardiac pacing lead has an adherent porous metal coating. The porous metal coating comprises metal particles joined to adjacent particles to define a plurality of connected interstitial pores uniformly distributed throughout the coating. A plurality of biodegradable fins adjacent to the electrode tip is the means for temporary attachment of the pacer lead to the surface of the heart. After surgical introduction, temporary fixation of the device is supplied by the fins. The device achieves permanent fixation by ingrowth of viable tissue into the interstices of the porous electrode. Such growth is blood and tissue compatible and involves very little scarring or fibrous tissue reaction. The process of permanent fixation occurs over a period of weeks during which time the fins are gradually absorbed into the blood and tissue, resulting in little, if any, fibrotic growth in the region of the electrode.

DESCRIPTION OF PREFERRED EMBODIMENT

Figure 2:
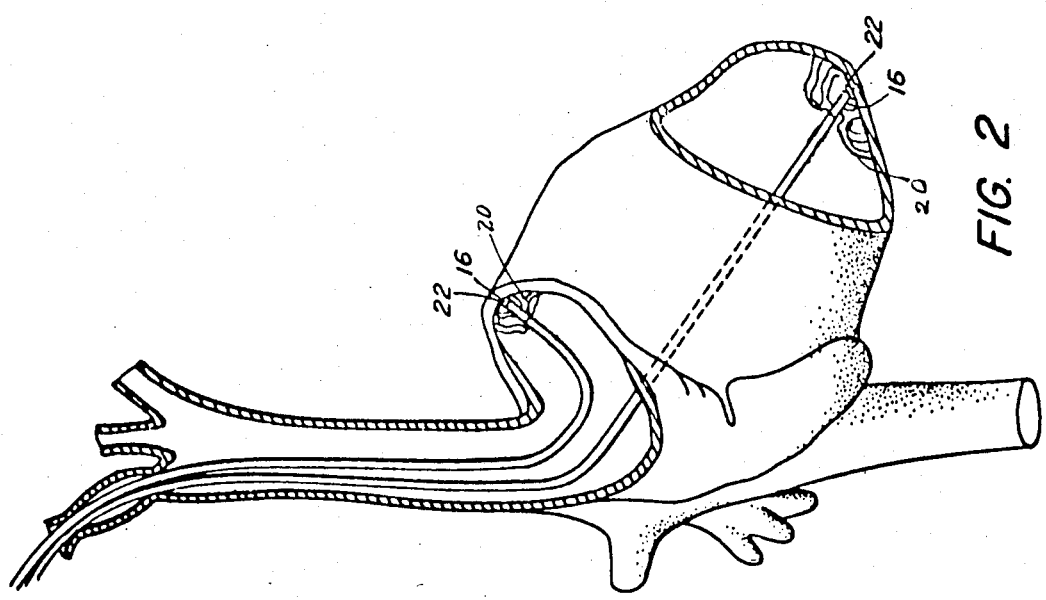
FIG. 2 is a diagrammatic view of a heart with parts broken away showing a ventricular lead and an atrial lead in their chronic state.
Figure 1:
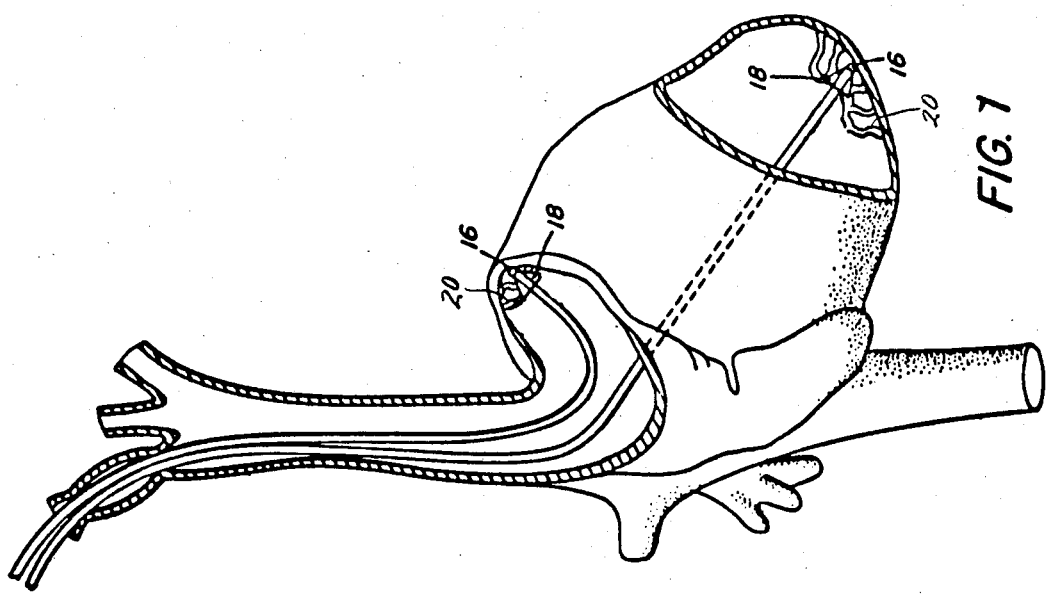
FIG. 1 is a diagrammatic view of a heart with parts broken away showing a ventricular pacing lead and an atrial pacing lead at implant.
Figure 3:
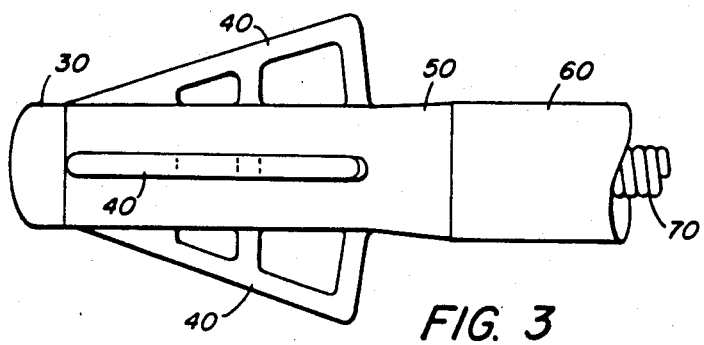
FIG. 3 is a side view of a distal lead assembly embodying the invention.
Figure 4:
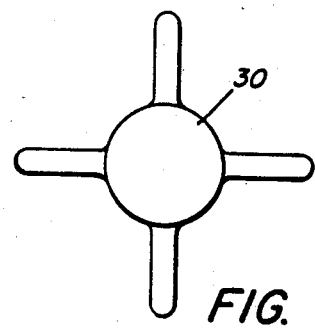
FIG. 4 is an end view of a distal lead assembly embodying the invention.
Figure 5:
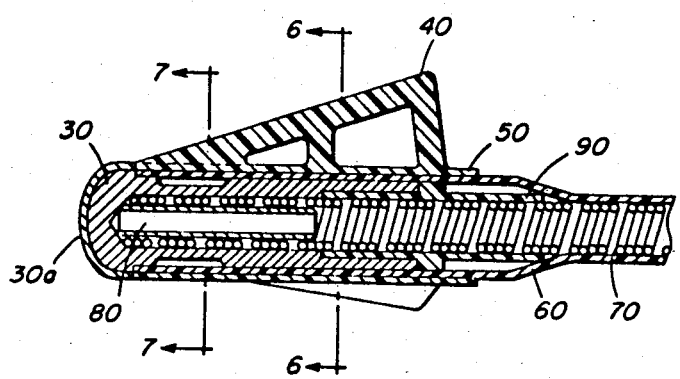
FIG. 5 is a sectional view of a distal lead assembly embodying the invention.
Figure 6:
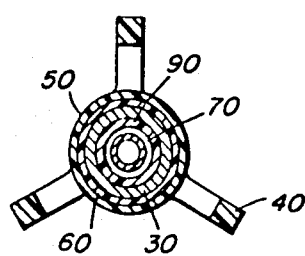
FIG. 6 is a cross sectional view taken across section line 6 of FIG. 5.
Figure 7:
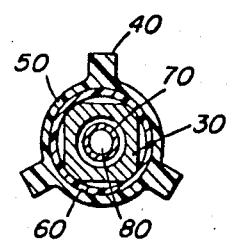
FIG. 7 is a cross sectional view taken along section line 7 of FIG. 6.

FIG. 1 is a diagrammatic view of the heart with parts broken away showing the atrial and ventricular leads at implant, with the porous electrode tips 16 in contact with the heart wall, the fins 18 ensnared in the trabeculi 20. FIG. 2 shows the chronic position of the leads after the fins have dissolved, the porous tips securing the leads, by a thin layer of fibrous tissue 22, which occurs within several weeks. As the porous electrode tip is "seen" by the heart as "friendly" and compatible, the resultant tissue growth minimizes the adverse reactions associated with the prior art. Thus, minimal tissue scarring and fibrous growth takes place to interfere with electrical transmission or to make subsequent removal difficult.

Referring now to FIGS. 3–7, a preferred embodiment of the present invention, there is shown a fin member comprising fins 40 and cylindrical supporting portion 50. Absorbable non-conducting, pliable rearwardly-projecting fins 40 are situated in close proximity to the electrode tip, so as to enable them to temporarily hold the lead in place, yet not interfere with the growth of tissue at the tip. The actual temporary fixation means may be single or multiple and is not necessarily restricted to fins but could include other designs such as tines, barbs, hooks, staples, sutures, balloons and helical coils.

Materials used for the fin member are similar or identical to those used for absorbable sutures in routine use in surgery, such as treated cat gut. The preferred material for the fin member is a copolymer of "Vicryl," a known suture material made by Ethicon consisting of a copolymer of glycolic and lactic acid, and polycaprolactone. Copolymerization with polycaprolactone serves to slow down degradation and to enhance flexibility.

The fins 40 are to be tapered and of ribbed design so that absorption occurs from their trailing edge tips inward toward the supporting portion 50 and forward toward the tip 30 so that loose pieces will not break off. The span of the fins will be small enough that, together with their pliable construction and tapered design, they will not interfere with implantation.

The metal electrode has a bulbous rounded "Elgiloy" (a metal alloy made by Elgiloy Company) tip 30 and an "Elgiloy" shank portion. The conducting tip 30 may be smooth or have a porous coating on its surface 30a, which coating consists of a layer of sintered "Elgiloy" beads. An alternate electrode material is platinum-iridium. Carbon can also be used as an electrode material, although metal is the preferred electrode material.

The resilient insulating sleeve 90 stretches over the coil and is positioned inside the electrode 30. The sleeve 90 serves to strengthen the joint and acts as a strain relief to protect the joint. The sleeve 90 is preferably made from a polyurethane, such as Pelethane ™, but can be made from other materials such as silicone.

A flexible non-conducting polyurethane sheath 60 houses the "Elgiloy" coil 70 through which the stylet is inserted in the conventional manner. The sheath 60 extends over the length of the pacing lead. The sheath is expanded over the full length of the shank portion of the electrode and bonded in place. The sheath is then coated with a cyanoacrylate adhesive, superbonder 410 from Loctite Corp. The compression molded fin member is then slipped over the electrode into its place behind the tip of the electrode. An alternate approach is to stick the end of the electrode into a mold and mold the fins right onto it at that time. An alternate material for the sheath 60 is silicone rubber. Alternate materials for the coil 70 are other metal alloys and carbon.

The coil 70 has inside of it a metal staking pin 80 in order to crimp the shank around the coil without crushing the coil. The coil is inserted into the end of the electrode and the electrode is then crimped over the staking pin.

The coil 70 is in electrical conduct with the electrode tip 30. The electrical current flows from the pacer, typically implanted in the shoulder region (not shown) via the coil 70 to the tip 30.

The lead of this invention which has been described in reference to pacemaker applications is equally effective as a tissue stimulation lead for other stimulations within the body, such as stimulation of the central or peripheral nervous system.

While this invention has been described with reference to its preferred embodiment, other embodiments can achieve the same result. Variations and modifications of the present invention will be obvious to those skilled in the art and it is intended to cover in the appended claims all such modifications and equivalents as fall within the time spiral and scope of this invention.

I claim:

1. A pervenous cardiac pacing lead, which comprises:
   an electrically insulating, flexible tubing having proximal and distal ends, said tubing being sized for pervenous introduction into the interior of a heart;
   electrical conductor means within said tubing for carrying electrical current therein between said proximal and distal ends of said tubing;
   electrically conductive tip means at said distal end and being in electrical contact with said conductor means for delivering electrical stimulation inside the heart, said tip means including means for enabling long term fixation in the heart; and
   a plurality of non-tissue penetrating, flexible, biodegradable projections extending outwardly from the side of said tubing for temporarily fixing the distal end of said tubing inside the heart, said biodegradable projections being absorbed over a period of time into blood or tissue of the body as said tip means becomes fixed in place.

2. A pervenous cardiac pacing lead as described in claim 1, in which said fixation enabling means includes a porous surface exposed on the distal end of said tubing to enable long term fixation of said tip means in place as a result of ingrowth of tissue into said porous surface.

3. A pervenous cardiac pacing lead as described in claim 1, in which said fixation enabling means includes at least an outer layer of porous conductive material having interstices into which heart tissue can grow for long term fixation of said tip means in the heart without subjecting the adjacent heart tissue to trauma and with a minimal amount of fibrotic tissue growth developing at the interface between said tip means and the adjacent heart tissue.

4. A pervenous cardiac pacing lead as described in claim 1, in which said biodegradable projections are solid but pliant and extend outwardly from said tubing at a position rearwardly of said tip means so that said biodegradable projections do not interfere with the long term fixation of said tip means in the heart.

5. A pervenous cardiac pacing lead as described in claim 1, in which said fixation enabling means includes at least an outer layer of porous conductive material on said tip means having interstices into which heart tissue can grow for long term fixation of said tip means in the heart without subjecting the adjacent heart tissue to trauma and with a minimal amount of fibrotic tissue growth developing at the interface between said tip means and the adjacent heart tissue; said biodegradable projections being solid but pliant and extending outwardly from said tubing at a position rearwardly of said tip means so that said biodegradable projections do not interfere with the long term fixation of said tip means in the heart.

6. A pervenous cardiac pacing lead as described in claim 1, wherein said biodegradable projections comprise a copolymer of a copolymer of glycolic and lactic acid and polycaprolactone.

7. A pervenous cardiac pacing lead as described in claim 1, in which said flexible tubing has approximately the same diameter throughout its length.

8. A pervenous cardiac pacing lead as described in claim 1, in which said biodegradable projections each have a generally triangular fin shape.

9. A pervenous cardiac pacing lead comprising:

an electrically insulating, flexible tubing having proximal and distal ends, said tubing being sized for pervenous introduction into the interior of a heart;

electrical conductor means within said tubing for carrying electrical current therein between said proximal and distal ends of said tubing;

porous electrically conductive tip means at said distal end having at least a porous surface exposed on the distal end of said tubing for enabling long term fixation in the heart and being in electrical contact with said conductor means for delivering electrical stimulation inside the heart; and non-tissue penetrating, flexible, biodegradable anchoring means including at least one generally triangular, fin-shaped projection fixed on and projecting outwardly from the side of said tubing for temporarily fixing the distal end of said tubing inside the heart, said biodegradable anchoring means being absorbed over a period of time into the blood or tissue of the body as said tip means becomes fixed in place as a result of ingrowth of tissue into said porous surface.

10. A pervenous cardiac pacing lead comprising:

an electrically insulating, flexible tubing having a central lumen and proximal and distal ends, said tubing being sized for pervenous introduction into the interior of a heart;

electrical conductor means within said central lumen of said tubing for carrying electrical current therein between said proximal and distal ends of said tubing;

electrically conductive tip means at said distal end in electrical contact with said conductor means for delivering electrical stimulation inside the heart;

said tip means including first anchoring means for long term anchoring of said tip means in the heart, said first anchoring means being disposed on said tip means;

second anchoring means for short term anchoring of said tip means in the heart, said second anchoring means comprising a plurality of solid but pliant, non-tissue-penetrating biodegradable projections fixed on and extending outwardly from a side of said tubing for temporarily fixing said tip means in the heart and for holding said tip means against a wall of the heart upon initial insertion of said tip means in the heart;

said biodegradable projections extending outwardly from said tubing at a position rearwardly of said tip means so that said biodegradable porjections do not interfere with long term anchoring of said tip means;

said biodegradable projections being absorbed over a short period of time by heart tissue so that, after said short time period, there are substantially no projections protruding outwardly from the outer surface of said tubing at said distal end of said tubing, and said distal end of said tubing can be pulled through a lumen formed in tissue surrounding the distal end of said tubing to pull said tip away from and out of engagement with the heart wall to which it is attached without any engagement of projections on the outer surface of said distal end of said tubing with the tissue wall of the lumen thereby to minimize trauma to heart tissue during removal of said lead and to facilitate removal of said lead.

11. A pervenous cardiac pacing lead as described in claim 10, in which said flexible tubing has approximately the same diameter throughout its length.

12. A pervenous cardiac pacing lead as described in claim 10, in which said first anchoring means comprises an outer layer of porous conductive material disposed on said tip means and having interstices into which heart tissue can grow for fixing said tip means in the heart without subjecting the adjacent heart tissue to trauma and with a minimal amount of fibrotic tissue growth developing at the interface between said tip means and the adjacent heart tissue.

13. A pervenous cardiac pacing lead as described in claim 12, wherein said tip means is only porous in a conductive surface layer thereof, and whereby said biodegradable projections temporarily anchor said distal end allowing ingrowth of tissue into said conductive surface layer to achieve long term fixation.

14. A pervenous cardiac pacing lead as described in claim 10, in which said biodegradable projections comprise a plurality of generally triangular-shaped fins.

15. A pervenous cardiac pacing lead as described in claim 10, wherein said biodegradable projections comprise a copolymer of a copolymer of glycolic and lactic acid and polycaprolactone.

16. A pervenous cardiac pacing lead as described in claim 10, wherein said biodegradable projections are attached to said tubing adjacent the distal end thereof and project radially outwardly and rearwardly from said distal end, whereby upon insertion of said distal end into the heart, said projections become entangled therein and eventually dissolve while temporarily anchoring said distal end.

* * * * *